United States Patent [19]

Jarman et al.

[11] Patent Number: 4,490,467

[45] Date of Patent: Dec. 25, 1984

[54] **POLYSACCHARIDE PRODUCTION USING NOVEL STRAINS OF *PSEUDOMONAS MENDOCINA***

[75] Inventors: Trevor R. Jarman, Haslingfield; Andrew J. Hacking, Reading, both of England

[73] Assignee: Kelco Biospecialties Ltd., London, England

[21] Appl. No.: 437,604

[22] Filed: Oct. 29, 1982

[30] Foreign Application Priority Data

Nov. 2, 1981 [GB] United Kingdom ............... 8132783

[51] Int. Cl.³ .................... C12P 19/04; C12N 1/20; C12R 1/38; C08B 37/04
[52] U.S. Cl. .................................. 435/101; 435/137; 435/138; 435/142; 435/232; 435/245; 435/253; 435/874; 536/3
[58] Field of Search ............. 536/3; 435/101, 137, 435/138, 142, 232, 245, 253, 874

[56] References Cited

U.S. PATENT DOCUMENTS

| | | | |
|---|---|---|---|
| 3,346,463 | 10/1967 | Goren | 435/101 |
| 3,856,625 | 12/1974 | Imrie | 435/101 |
| 4,235,966 | 11/1980 | Jarman et al. | 435/101 |
| 4,298,725 | 11/1981 | Williams et al. | 435/101 |

OTHER PUBLICATIONS

Govan et al., "Isolation of Alginate-producing Mutants of *Pseudomonas fluorescens, Pseudomonas putida* and *Pseudomonas mendocina*", Jour. of Gen. Microbiol., vol. 125, pp. 217–220, (1981).

Palleroni et al., "Taxonomy of the Aerobic Pseudomonads: the Properties of the *Pseudomonas stutzeri* Group", Jour. of Gen. Microbiol., vol. 60, pp. 215–231, (1970).

Primary Examiner—Thomas G. Wiseman
Assistant Examiner—Deborah A. Grossman
Attorney, Agent, or Firm—Gabriel Lopez; Hesna J. Pfeiffer

[57] ABSTRACT

A process for producing polysaccharide consisting of a partially acetylated variable block copolymer of D-mannuronic and L-guluronic acid residues comprises growing a biologically pure culture of a *Pseudomonas mendocina* microorganism selected from the group consisting of NCIB 11687, 11688, and 11689 in an aqueous nutrient medium by submerged aerobic fermentation of an assimilable carbon source and recovering the polysaccharide. Biologically pure cultures of the organisms are another feature of the invention.

2 Claims, 1 Drawing Figure

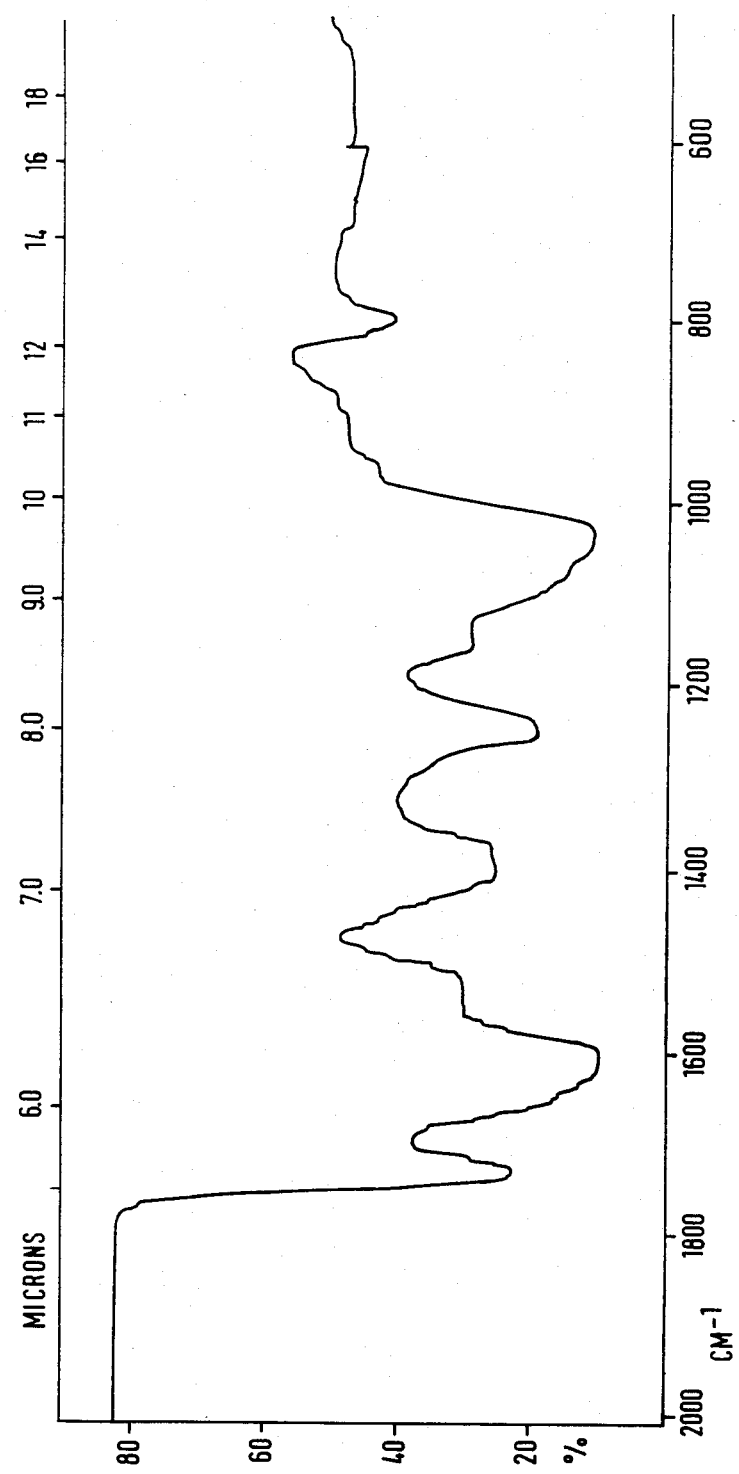

POLYSACCHARIDE PRODUCTION USING NOVEL STRAINS OF *PSEUDOMONAS MENDOCINA*

This invention relates to a process for the production of polysaccharide of the alginate type from a microbial source other than *Azotobacter vinelandii*.

Alginic acid, a hydrophilic colloidal carbohydrate acid, is a variable block copolymer composed of D-mannuronic and L-guluronic acid units. Alkali salts of alginic acid are soluble in water and one of the outstanding characteristics of such alginate solutions is their high viscosity at low concentrations. Addition of divalent ions such as calcium or magnesium ions to the solutions causes gelation. The unique physical properties of alginates give them a wide range of industrial applications as emulsifiers, stabilizers and thickeners. They are of particular use in the food industry, in pharmaceuticals, in paper and textile processing and in agriculture.

Alginates and alginic acid have been commercially obtained by extraction from certain species of seaweed. An alternative source is the microbial alginate producer *Azotobacter vinelandii*. Another microorganism which has been noted to produce polysaccharide of the alginate type is *Pseudomonas aeruginosa*. The polysaccharide produced by *A. vinelandii* and *P. aeruginosa* is similar to that obtained from seaweeds except that the molecule is partially acetylated.

However, certain problems arise in the production of alginates from *Azotobacter vinelandii*. Strict controls on the fermentation are necessary in order to produce a viscous polymer in high yield at a suitable concentration. On the other hand, *Pseudomonas aeruginosa* is undesirable as a source since it is associated as a secondary infection in cystic fibrosis patients. Other species of Pseudomonas such as *P. putida* and *P. mendocina* which might be safe sources do not usually produce significant amounts of exopolysaccharide and so cannot normally be used.

U.K. Patent application No. 2 026 515A discloses a process for the production of such a polysaccharide which involves treating a normally non-mucoid species of Pseudomonas with a β-lactam or amino-glycoside antibiotic in order to select a strain tolerant to said antibiotic, which tolerant strain is a polysaccharide producer. That process makes available strains of non-pathogenic pseudomonads which, unusually, are polysaccharide producers. A problem which remains, however, is the lack of stability of the strains. It has so far proved impossible to select by this process a strain of a normally non-mucoid pseudomonad which will remain stable, i.e. polysaccharide-producing, for a sufficient length of time in a continuous fermentation apparatus to permit an industrial process to be carried out.

We have now obtained 3 new strains of *Pseudomonas mendocina* which produce good yields of the desired polysaccharide and which are stable in continuous fermentation.

According to the present invention there is provided a process for the production of a polysaccharide consisting of a partially acetylated variable block copolymer of D-mannuronic and L-guluronic acid residues, which comprises cultivating in a nutrient medium therefor a biologically pure culture of *Pseudomonas mendocina* strain NCIB 11687, 11688 or 11689 and isolating from the medium the polysaccharide produced. There is also provided a biologically pure culture of a *Pseudomonas mendocina* microorganism selected from the group consisting of NCIB 11687, 11688, and 11689; and a culture containing a *Pseudomonas mendocina* organism selected from the group consisting of NCIB 11687, 11688, and 11689, said culture being capable of producing polysaccharide consisting of a partially acetylated variable block copolymer of D-mannuronic and L-guluronic acid residues in recoverable amounts by submerged, aerobic fermentation of an assimilable carbon source. The above-mentioned new strains were obtained as follows. *P. mendocina* NCIB 10541 was exposed to carbenicillin at levels above the minimum inhibitory concentration (MIC) and resistant polysaccharide-producing strains were selected. The process was that disclosed in U.K. Application No. 2 026 515A. Thus, a culture of *P. mendocina* NCIB 10541 in the log phase of growth, in a nutrient broth, was serially diluted and spread onto nutrient agar plates containing carbenicillin (Beechams Pharmaceuticals, Worthing) initially in the range of 0 to 1,000 mg $l^{-1}$ in multiples of 100 mg $l^{-1}$. This gave an approximate indication of the MIC which was defined further by a second set of determinations over a narrower range in multiples of 20 mg $l^{-1}$. Serial dilutions of a log phase culture of *P. mendocina* NCIB 10541 in nutrient broth were spread over nutrient agar plates containing 1.5 times the MIC of carbenicillin. The plates were examined after 36 hours incubation at 30° C. and resistant mucoid clones were selected on the basis of their raised, glistening appearance and were purified by being grown on minimal agar (a salts medium containing no C source: Jayasuria GCN 1955 *J. Gen. Microbiol.* 12 419–28) to which had been added 2% glucose.

These selectant strains were then contacted with a mutagenic agent as follows. A culture of the selectant in the log phase of growth was harvested by centrifugation, washed in 0.5M tris-maleate buffer at pH 6.0 and resuspended in 9 ml of this buffer to a density of $0.5 \times 10^9$ cells $ml^{-1}$. N-methyl-N-nitro-nitrosoguanidine (Sigma Chemicals) dissolved in the same buffer was added to a final concentration of 20 mg $l^{-1}$. The mixture was incubated for 30 minutes at 30° C. and the cells were then harvested by centrifugation, washed in minimal salts medium and resuspended in 100 ml of a salts medium containing 1% glucose. The most promising strain from the carbenicillin enrichment was exposed to the mutagen. This mutation produced a number of very large mucoid clones which were purified and analysed for polysaccharide production in shake flask culture. The most promising were selected and deposited under Nos. 11687, 11688 and 11689 at the National Collection of Industrial Bacteria on Oct. 22, 1981. The most stable, and hence most preferred, strain is NCIB 11687.

The strains of use according to the present invention are exopolysaccharide producing strains of *Pseudomonas mendocina* and possess the following characteristics:

Rods, 0.7–0.8 by 1.4–2.8 μm, occurring singly and in pairs. Motile with predominantly monotrichous polar flagellation. Do not produce sheaths or prosthecae. Gram negative.

Colonies yellowish as a result of production of intracellular carotenoid pigment; some adherence. No diffusible pigments produced.

Egg yolk reaction negative. Catalase positive.

Organic growth factors not required. Can utilize various organic compounds as sole carbon sources for growth including arginine, geraniol, glycollate, ethylene glycol, propylene glycol and sarcosine; pentoses, hexoses other than glucose and fructose disaccharides and mannitol not used.

Obligately aerobic, except in media with nitrate. Growth at 41° C. but not 4° C. Optimal temperature for growth ca. 35° C.

They also are specifically characterised in that they produce exopolysaccharide as a capsule. The following table compares the new strains with the type strain of *P. mendocina* (NCIB 10541) and with *P. aeruginosa*.

TABLE 1

|  | P. aeruginosa | P. mendocina (Bergey 1974) | Strains NCIB 11687 11688 11689 |
|---|---|---|---|
| No. of *flagella* | 1 | 1 | 1 |
| Fluorescent pigments | d | — | — |
| Pyocyanine | d | — | — |
| Carotenoids | — | + | + |
| Growth at 41° C. | + | + | + |
| Levan formation from sucrose | — | — | — |
| Arginine dihydrolase | + | + | + |
| Oxidase reaction | + | + | + |
| Denitrification | + | + | + |
| Hydrolysis of: |  |  |  |
| Gelatin | + | — | — |
| Starch | — | — | — |
| Poly-$\beta$-hydroxybutyrate | — | — | — |
| Carbon sources for growth: |  |  |  |
| Glucose | + | + | + |
| Trehalose | — | — | — |
| 2-Ketogluconate | + | — | — |
| meso-Inositol | — | — | — |
| Geraniol | + | + | + |
| L-Valine | + | + | + |
| $\beta$-Alanine | + | + | + |
| DL-Arginine | + | + | + |
| D-Ribose | + | — | — |
| Mannitol | + | — | — |
| 2-Oxoglutarate | + | — | — |
| Ethylene glycol | — | + | + |
| Azelate | + | — | + |
| Polysaccharide produced | + | — | + | d = positive for more than 10% but less than 90% of all strains studied.

The polysaccharide produced is a typical acetylated alginate as evidenced by the infrared spectrum shown in FIG. 1 accompanying this specification.

The process for production of polysaccharide according to the present invention can be effected in any pseudomonad-supporting medium. The process is conveniently effected in a continuous manner by continuous dilution of a fixed-volume steady-state fermenter well known in this art (see, e.g., Herbert, Elesworth and Telling, 1956, Journal of General Microbiology 14, 601). Typical media include complex broths, e.g., a 1% nutrient broth, or a chemically defined ("salts") medium with a supplementary carbon source e.g., an alcohol such as glycerol, a sugar such as glucose or a sugar acid such as gluconic acid. The cultivation temperature should be about 30° C. and the pH of the medium should be maintained at about 7.0 during continuous cultivation. The conditions must favour aerobic growth and we have found that optimal rates of polysaccharide production are obtained by maintaining the dissolved oxygen tension in the range 18 to 25% saturation. Below this range, polysaccharide concentration is reduced, while above this range, polysaccharide concentrations remain high but carbon conversion efficiencies (i.e. efficiency of conversion of the carbon source into polysaccharide) fall, presumably because of increased oxidation to carbon dioxide. Continuous cultivation is conveniently effected under nitrogen limitation, i.e. such that the nitrogen source in the medium is the limiting nutrient when the culture is at steady state.

We have found that the new strains of *P. mendocina* are capable of producing polysaccharide having good rheological properties. When the process as described above is effected, a low molecular weight product having relatively low viscosity is obtained having properties similar to a printing-grade alginate such as Manutex F (Alginate Industries Ltd). This low molecular weight product has a low pseudoplasticity which is also useful in printing applications. British Patent Specification No. 1 548 078 describes a process for producing a polysaccharide of the alginate type having an improved viscosity, by cultivation of *A. vinelandii* in the presence of a protease. The presence of a protease apparently deactivates or removes the alginate lyase produced by the microorganism, which is responsible for lowering the viscosity of the polysaccharide. The new strains of *P. mendocina* of use according to the present invention are not so seriously affected by the production of alginate lyase, but nevertheless we have found it helpful to include a protease in the medium during production of the polysaccharide. Any protease having the required action on alginate lyase can be utilized, although those most suitable are the proteases derived from microbial sources such as the bacterial and fungal proteases sold, e.g., by Novo Industri A/S of Copenhagen Denmark under the Trade Marks Alcalase and Neutrase. In continuous culture it is particularly preferred to use an enzyme which exhibits its optimum activity at a neutral or slightly alkaline pH. Addition of such a protease (e.g. at a level of about 0.1 to 2 Anson units per liter) leads to the production of a high molecular weight, high viscosity product having properties similar to Manutex R.S. (Alginate Industries Ltd).

The following examples illustrate the invention further:

EXAMPLES 1 TO 4

An LH Engineering Ltd type 1/1000 laboratory fermentation module fitted with a 5 liter fermentation vessel modified for continuous culture (working volume=2.5 l) was used. The medium used is described in Table 2. The fermentation pH was maintained at 7.0 by the automatic addition of 2M NaOH, and the temperature was set at 30° C. Foaming was controlled by the addition of a silicone antifoaming agent. Air was supplied at 1 l min$^{-1}$ and the culture was mixed at an impeller speed of 300–750 rpm so as to maintain the dissolved oxygen concentration at ca 20% of saturation. The medium was introduced into the fermenter and inoculated with 100 ml of a late log phase culture of strain NCIB 11687 grown in minimal medium containing 1% (w/v) glucose in a shake flask.

Addition of further medium was commenced when the batch culture reached the stationary phase. The dilution rate was adjusted to the desired figure by alteration of the rate of flow of the medium. The growth limiting nutrient was demonstrated by increasing the concentration of the nutrient twofold and by obtaining an increase in cell concentration.C Culture viscosity measurements were made using a Wells-Brookfield HAT cone and plate microviscometer at a temperature of 25° C. For continuous culture broths where protease was used, the HBT model was employed. The apparent viscosities were determined over a range of shear rates from 3.75 to 750 s$^{-1}$ and the consistency index K (apparent viscosity at a shear rate of 1 s$^{-1}$) was obtained by extrapolation of a log-log plot of apparent viscosity against shear rate.

A more detailed rheological examination of samples obtained from continuous culture broths was made using a Contraves Rheomat-30 rotational viscometer with a cone and plate system. A 1% polysaccharide solution in (a) distilled water and (b) EDTA/100 mM) was prepared by continuous agitation for 1 h using a Citenco top-stirrer. Solutions were examined at 30 shear rates and consistency indices and flow behaviour indices (c) obtained from shear rate versus viscosity plots.

Bacterial cells and exopolysaccharide could only be separated in the presence of a chelating agent. Culture broth (40 ml) was mixed with 5M NaCl (0.8 ml) and 0.5M Na$_4$ EDTA (0.8 ml) and after standing for 10 minutes was centrifuged at 24000 g for 40 min. The supernatant was removed and 25 added to 75 ml isopropanol. After mixing and standing for 10 min the precipitate obtained was filtered on a pre-weighed glass fibre disc (whatman GF/A) which was dried in vacuo for 24 h and re-weighed.

The results are summarised in Tables 3 and 4. Similar results are obtained with strains NCIB 11688 and 11689.

EXAMPLE 5

Effect of Protease Addition

The culture conditions described for Example 4 were repeated but using media containing various amounts of Neutrase (Novo Industri A/S). The rheology of the products is described in Tables 5 and 6.

TABLE 2

| Continuous culture medium | |
|---|---|
| (NH$_4$)$_2$ HPO$_4$ | 1.25 gl$^{-1}$ |
| K$_2$HPO$_4$ | 1.25 gl$^{-1}$ |
| Ca(OH)$_2$ | 0.05 gl$^{-1}$ |
| Mg (OH)$_2$ | 0.07 gl$^{-1}$ |
| Mg SO$_4$ 7H$_2$O | 0.15 gl$^{-1}$ |
| Citric acid | 0.99 gl$^{-1}$ |
| Yeast extract | 0.2 gl$^{-1}$ |
| MnSO$_4$ 4H$_2$O | 1.1 mgl$^{-1}$ |
| FeSO$_4$ 7H$_2$O | 3.56 mgl$^{-1}$ |
| 2nSO$_4$ 7H$_2$O | 0.7 mgl$^{-1}$ |
| Cu SO$_4$ 5H$_2$O | 0.25 mgl$^{-1}$ |
| Co SO$_4$ 7H$_2$O | 0.28 mgl$^{-1}$ |
| H$_3$BO$_4$ | 0.06 mgl$^{-1}$ |
| Dexyme | 112 gl$^{-1}$ |
| (Glucose by analysis | 90 gl$^{-1}$) |

TABLE 3

Polysaccharide production by *P. mendocina* NCIB 11687 at steady state conditions

| | Example | | |
|---|---|---|---|
| | 1 | 2 | 3 |
| Time (h) | 148.5 | 101.5 | 5.5 |
| Dilution rate (h$^{-1}$) | 0.03 | 0.04 | 0.06 |
| Cell dry weight (gl$^{-1}$) | 1.5 | 1.4 | 1.35 |
| Total precipitatable matter (T.P.M.) (gl$^{-1}$) | 17.5 | 1.4 | 1.35 |
| Cell: polysaccharide ratio | 10.6 | 11.8 | 16.4 |
| Glucose concentration in feed (gl$^{-1}$) | 90 | 90 | 90 |
| Residual glucose (gl$^{-1}$) | 33.5 | 32.0 | 25.5 |
| Yield of polysaccharide (yps) | 0.31 | 0.31 | 0.36 |
| Dissolved oxygen (approx. %) | 20 | 20 | 20 |

TABLE 4

Stability of strain NCIB 11687 in continuous culture

| Time of fermentation (h) | T.P.M.gl$^{-1}$ | Percentage of small colonies |
|---|---|---|
| 0 | 0 | 0 |
| 25.6 | 15.6 | 0 |
| 52 | 19.0 | 5 |
| 121.5 | 15.1 | 5 |
| 196.5 | 18.5 | 17 |
| 297.5 | 20.3 | 21 |
| 381 | 18.4 | 35 |

Dilution rate was maintained at an average of 0.05h$^{-1}$. The medium was the nitrogen limited formula (Table 2).

TABLE 5

Effect of Neutrase on culture viscosity

| Neutrase (Anson Units l$^{-1}$) | 0 | 0.1 | 0.25 |
|---|---|---|---|
| TPM gl$^{-1}$ | 18.5 | 21 | 19.6 |
| Cell dry weight gl$^{-1}$ | 1.9 | 2.0 | 1.65 |
| Culture consistency index | 32 | 4,700 | 5,100 |

TABLE 6

Rheology of products obtained

| Sample | Solvent | Consistency index (K) | Flow behaviour index (n) |
|---|---|---|---|
| Nitrogen limited Culture without protease | H$_2$O | 9.6 | 0.86 |
| | 100 m MEDTA | 8.4 | 0.86 |
| Nitrogen limited Culture plus protease | H$_2$O | 8,043 | 0.27 |
| | 100 m MEDTA | 557 | 0.43 |
| Manutex F (Alginate Industries) | H$_2$O | 31.4 | 0.91 |
| | 100 m MEDTA | 12.8 | 0.98 |

All samples were prepared as 1% solutions
Culture broths were precipitated with isopropanol (75%), precipitates collected by filtration and dried under an infra-red lamp.

We claim:

1. A biologically pure culture of a *Pseudomonas mendocina* microorganism selected from the group consisting of NCIB 11687, 11688, and 11689, said culture being capable of producing polysaccharide consisting of a partially acetylated variable block copolymer of D-mannuronic and L-guluronic acid residues in recoverable amounts by submerged, aerobic fermentation of an assimilable carbon source.

2. In a process for producing polysaccharide consisting of a partially acetylated variable block copolymer of D-mannuronic and L-guluronic acid residues which comprises growing a biologically pure culture of a *Pseudomonas mendocina* microorganism in an aqueous nutrient medium by submerged aerobic fermentation of an assimilable carbon source and recovering said polysaccharide, the improvement which comprises said *P. mendocina* microorganism being selected from the group consisting of NCIB 11687, 11688, and 11689.

* * * * *